(12) United States Patent  
Kirschman

(10) Patent No.: US 8,945,227 B2
(45) Date of Patent: Feb. 3, 2015

(54) SPINAL IMPLANT CO-INSERTION SYSTEM AND METHOD

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 380 days.

(21) Appl. No.: 13/017,622

(22) Filed: Jan. 31, 2011

(65) Prior Publication Data

US 2011/0190892 A1     Aug. 4, 2011

Related U.S. Application Data

(60) Provisional application No. 61/300,102, filed on Feb. 1, 2010.

(51) Int. Cl.
*A61F 2/44*       (2006.01)
*A61F 2/46*       (2006.01)
*A61B 17/70*    (2006.01)

(52) U.S. Cl.
CPC . *A61B 17/70* (2013.01); *A61F 2/44* (2013.01); *A61F 2/46* (2013.01)
USPC .......................................... 623/17.16; 606/99

(58) Field of Classification Search
USPC ............ 623/17.11–17.16; 606/99–100, 86 A, 606/914
See application file for complete search history.

(56) References Cited

U.S. PATENT DOCUMENTS

| | | |
|---|---|---|
| 5,423,825 A | 6/1995 | Levine |
| 5,423,826 A | 6/1995 | Coates et al. |
| 5,522,899 A | 6/1996 | Michelson |
| 5,599,279 A | 2/1997 | Slotman et al. |
| 5,653,761 A | 8/1997 | Pisharodi |
| 5,722,977 A | 3/1998 | Wilhelmy |
| 5,782,919 A | 7/1998 | Zdeblick et al. |
| 5,888,224 A | 3/1999 | Beckers et al. |
| 6,030,390 A | 2/2000 | Mehdizadeh |
| 6,039,761 A | 3/2000 | Li et al. |
| 6,042,582 A | 3/2000 | Ray |
| 6,063,088 A | 5/2000 | Winslow |
| 6,066,174 A | 5/2000 | Farris |
| 6,074,390 A | 6/2000 | Zucherman et al. |
| 6,083,225 A | 7/2000 | Winslow et al. |
| 6,093,207 A | 7/2000 | Pisharodi |
| 6,096,038 A | 8/2000 | Michelson |
| 6,113,602 A | 9/2000 | Sand |
| 6,139,551 A | 10/2000 | Michelson et al. |
| 6,159,215 A | 12/2000 | Urbahns et al. |
| 6,174,311 B1 | 1/2001 | Branch et al. |
| 6,210,412 B1 | 4/2001 | Michelson |
| 6,224,607 B1 | 5/2001 | Michelson |
| 6,235,059 B1 | 5/2001 | Benezech |
| 6,261,296 B1 | 7/2001 | Aebi et al. |
| 6,267,763 B1 | 7/2001 | Castro |
| 6,270,498 B1 | 8/2001 | Michelson |
| 6,319,257 B1 | 11/2001 | Carignan et al. |
| 6,432,106 B1 * | 8/2002 | Fraser ........................ 623/17.11 |
| 6,478,796 B2 | 11/2002 | Zucherman et al. |
| 6,478,800 B1 | 11/2002 | Fraser et al. |

(Continued)

*Primary Examiner* — Todd Manahan
*Assistant Examiner* — Eric S Gibson
(74) *Attorney, Agent, or Firm* — Jacox, Meckstroth & Jenkins

(57) ABSTRACT

A system and method for substantially simultaneous co-insertion of an implant, such as a cage and plate. An inserter is secured to the cage and plate and is used to hold the components while implanting the components during a surgical procedure.

21 Claims, 5 Drawing Sheets

(56) References Cited

U.S. PATENT DOCUMENTS

| | | |
|---|---|---|
| 6,576,017 B2 | 6/2003 | Foley et al. |
| 6,610,065 B1 | 8/2003 | Branch et al. |
| 6,635,087 B2 | 10/2003 | Angelucci et al. |
| 6,652,533 B2 | 11/2003 | O'Neil |
| 6,666,866 B2 | 12/2003 | Martz et al. |
| 6,770,074 B2 | 8/2004 | Michelson |
| 6,896,676 B2 | 5/2005 | Zubok et al. |
| 6,926,737 B2 | 8/2005 | Jackson |
| 6,972,019 B2 | 12/2005 | Michelson |
| 6,991,654 B2 | 1/2006 | Foley |
| 7,112,222 B2 * | 9/2006 | Fraser et al. ............... 623/17.11 |
| 7,163,561 B2 | 1/2007 | Michelson |
| 7,172,627 B2 | 2/2007 | Fiere et al. |
| 7,182,782 B2 | 2/2007 | Kirschman |
| 7,232,464 B2 | 6/2007 | Mathieu |
| 7,235,105 B2 * | 6/2007 | Jackson ................... 623/17.16 |
| 7,244,258 B2 | 7/2007 | Burkus et al. |
| 7,252,673 B2 | 8/2007 | Lim |
| 7,300,441 B2 | 11/2007 | Haid et al. |
| 7,537,603 B2 | 5/2009 | Huebner et al. |
| 7,547,306 B2 | 6/2009 | Michelson |
| 7,594,931 B2 | 9/2009 | Louis et al. |
| 7,618,456 B2 | 11/2009 | Mathieu et al. |
| 7,621,938 B2 | 11/2009 | Molz, IV |
| 7,628,816 B2 | 12/2009 | Magerl et al. |
| 7,637,911 B2 | 12/2009 | Zubok et al. |
| 7,637,952 B2 | 12/2009 | Landry et al. |
| 7,641,665 B2 | 1/2010 | Zubok et al. |
| 7,641,701 B2 | 1/2010 | Kirschman |
| 7,648,511 B2 | 1/2010 | Zubok et al. |
| 7,655,028 B2 | 2/2010 | Kirschman |
| 7,674,292 B2 | 3/2010 | Zubok et al. |
| 7,704,250 B2 | 4/2010 | Michelson |
| 7,740,630 B2 | 6/2010 | Michelson |
| 7,758,616 B2 | 7/2010 | LeHuec et al. |
| 7,815,681 B2 * | 10/2010 | Ferguson ................... 623/17.16 |
| 2006/0036250 A1 * | 2/2006 | Lange et al. ................ 606/69 |
| 2006/0195100 A1 | 8/2006 | Kirschman |
| 2007/0123885 A1 | 5/2007 | Kirschman |
| 2008/0021476 A1 | 1/2008 | Kirschman |
| 2008/0161925 A1 * | 7/2008 | Brittan et al. ............. 623/17.16 |
| 2008/0221695 A1 * | 9/2008 | Jacofsky et al. ........... 623/17.16 |
| 2008/0294262 A1 * | 11/2008 | Levieux .................... 623/17.16 |
| 2009/0012529 A1 * | 1/2009 | Blain et al. ................ 606/99 |
| 2009/0182430 A1 * | 7/2009 | Tyber et al. ............... 623/17.16 |
| 2010/0145453 A1 | 6/2010 | Kirschman |

\* cited by examiner

SPINAL IMPLANT CO-INSERTION SYSTEM AND METHOD

CROSS-REFERENCE TO RELATED APPLICATION

The present application claims priority to provisional U.S. application Ser. No. 61/300,102 filed Feb. 1, 2010, to which Applicant claims the benefit of the earlier filing date. This application is incorporated herein by reference and made a part hereof.

BACKGROUND OF THE INVENTION

1. Field of the Invention

This invention relates to spinal implants and, more particularly, to a co-insertion system and method for substantially simultaneously inserting or implanting a cage and plate in a patient during a surgical procedure.

2. Description of the Related Art

In order to stabilize two adjacent vertebrae of the spine, surgeons will typically place two components. The first is a bone-filled generally cuboidal device, termed a cage, in-between the adjacent vertebrae. The second is a plate device bridging the adjacent vertebrae and attached to the vertebrae via bone screws or similar means. The placement of these two devices is performed in a serial fashion with additive operative time. Additionally, different insertion instruments are utilized for the plate and cage components, resulting in increased cost, complexity and duplication.

Recently, there have been efforts to integrate the plate and cage components into either a unified or mechanically coupled device as exemplified by U.S. Pat. No. 6,235,059, which is incorporated herein by reference and made a part hereof. An advantage of such a unified device is that it creates efficiency for the surgeon by reducing the number of implantation steps and instruments. A disadvantage of such a device is that it doesn't allow for uncoupled motion between the cage and plate components, despite the fact that these components are subjected to differing biomechanical loads after implantation.

What is needed, therefore, is a combination cage-plate device with a co-inserter instrument that allows for loading of both implants on a single inserter and simultaneous co-implantation of separate plate and cage components. The inserter can be removed following implantation resulting in the appropriate positioning of the two independent and uncoupled components.

SUMMARY OF THE INVENTION

One object of the invention is to provide a combination cage-plate device with a co-inserter that allows for substantially simultaneous loading and placement of both the cage and plate on the co-inserter.

Another object of the invention is to provide a system and method for simultaneous co-implantation of the separate plate and cage components of an implant.

Still another object of the invention is to provide an inserter for inserting a cage and plate that can be removed following implementation of the two independent and un-coupled components.

In one aspect, one embodiment of the invention comprises a spinal implant co-insertion system comprising an inserter having a handle and an inserter fastener, a cage having at least one coupler adapted to be fastened to the inserter fastener a plate, the inserter being adapted to simultaneously receive the plate and the cage for simultaneous co-implantation of the plate and cage.

In another aspect, another embodiment of the invention comprises a plate for use in a spinal implant co-insertion system, comprising a body, the body having an internal wall that defines a through-hole for receiving an inserter having an inserter end that is screwed into a cage so that the inserter can simultaneously receive the cage and the plate so that they can be simultaneously implanted during a surgical procedure.

In still another aspect, another embodiment of the invention comprises a method for co-inserting a cage and a plate during a surgical procedure, the method comprising the steps of coupling an inserter to the cage and the plate so that the inserter simultaneously receives and supports the cage and plate, simultaneously implanting the cage and plate using the inserter during a surgical procedure, removing the inserter from the cage and removing the inserter from the plate.

These and other objects and advantages of the invention will be apparent from the following description, the accompanying drawings and the appended claims.

DETAILED DESCRIPTION OF PREFERRED EMBODIMENTS

Figure 1:
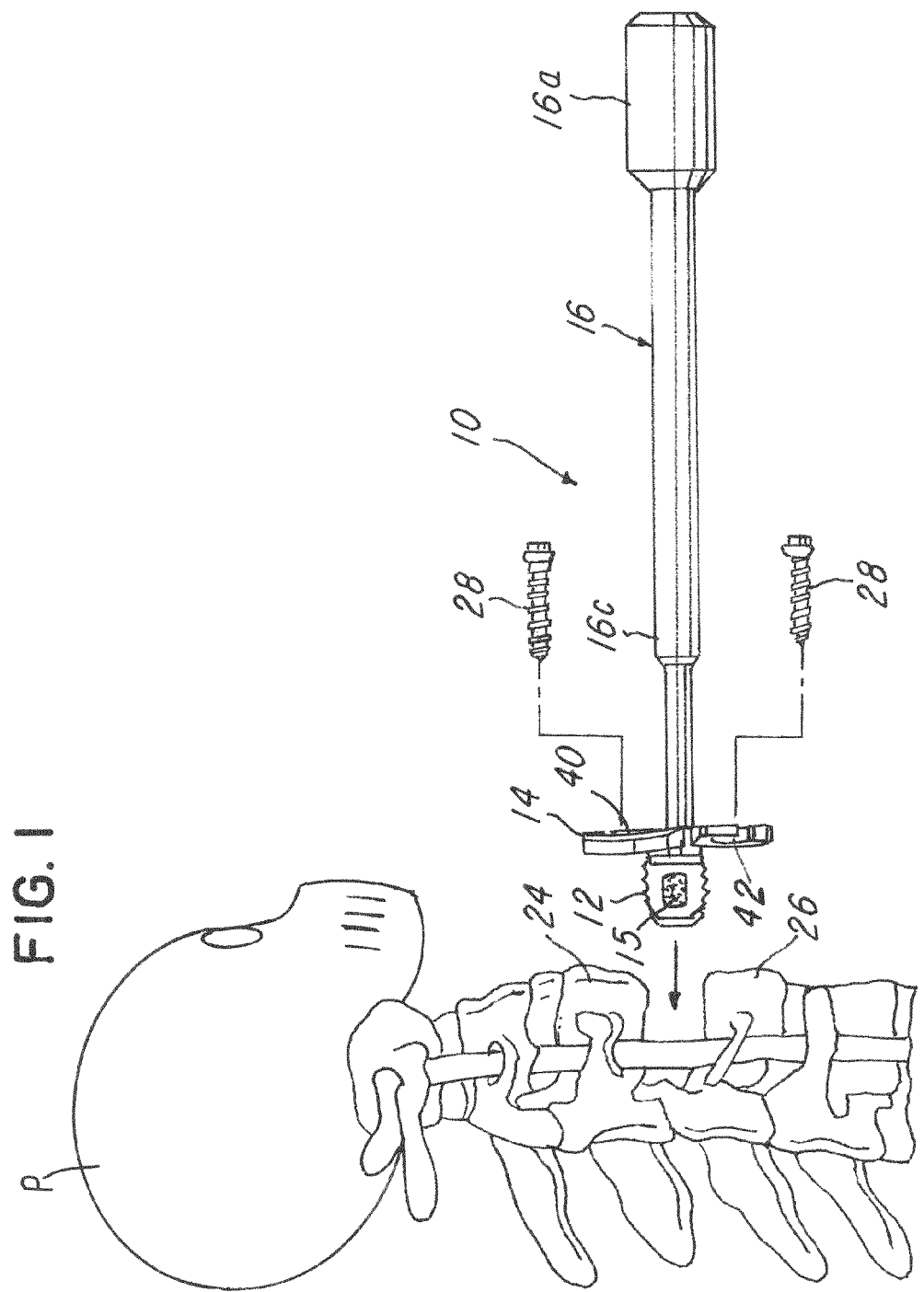
FIG. 1 is a view illustrating a system for co-insertion of an implant having a cage and plate during a surgical procedure in accordance with one embodiment of the invention.

Referring now to FIG. 1, a system and method 10 for substantially simultaneous co-insertion of a cage 12 and plate 14 with an inserter 16 are shown. The system 10 includes the inserter 16 which comprises a grip or first end 16a and a second end 16b that is threaded as described later herein.

The inserter 16 further comprises an integral elongated portion 16c which couples the first end 16a to the second end 16b.

The inserter 16 comprises a stop or shoulder 18. As described in more detail later herein, the shoulder 18 (FIG. 3) engages the plate 14 as described later herein.

Figure 7A:
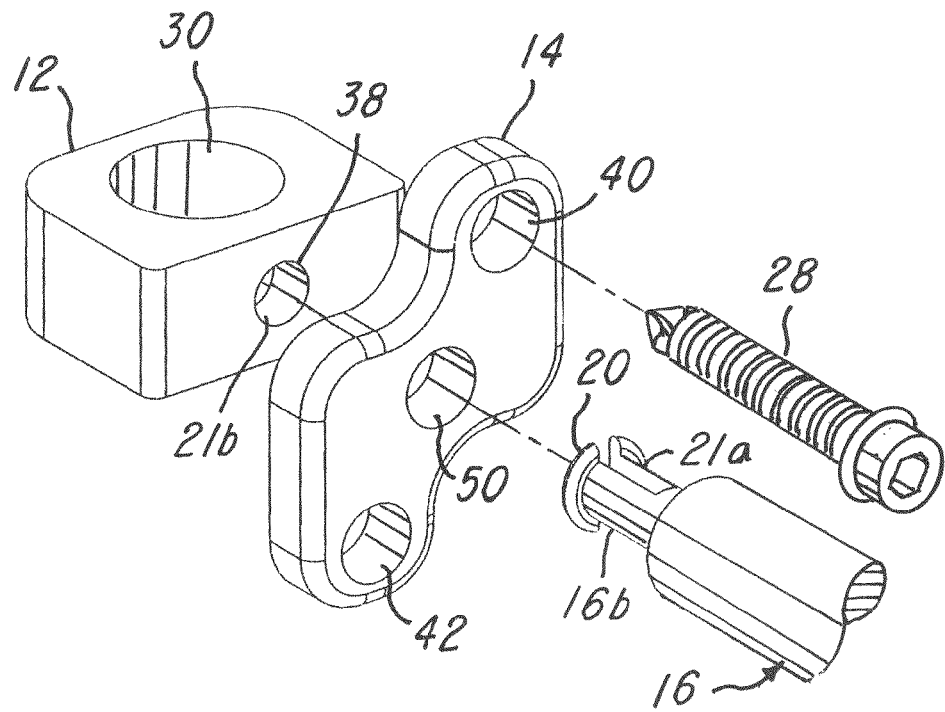
FIGS. 7A-7C are various fragmentary views illustrating different exemplary embodiments for fastening or coupling the inserter to the cage.
Figure 7B:
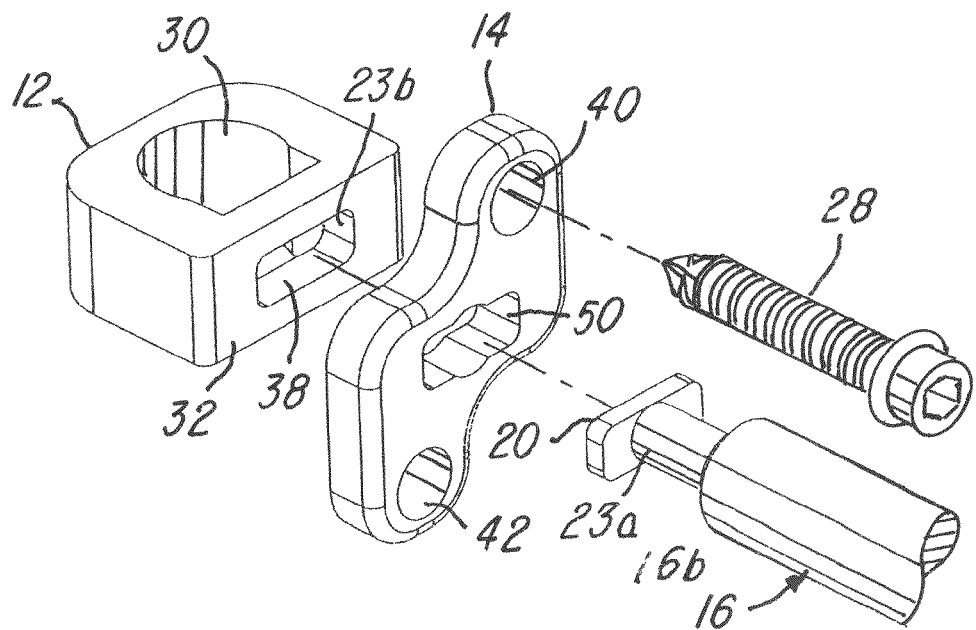
Figure 7C:
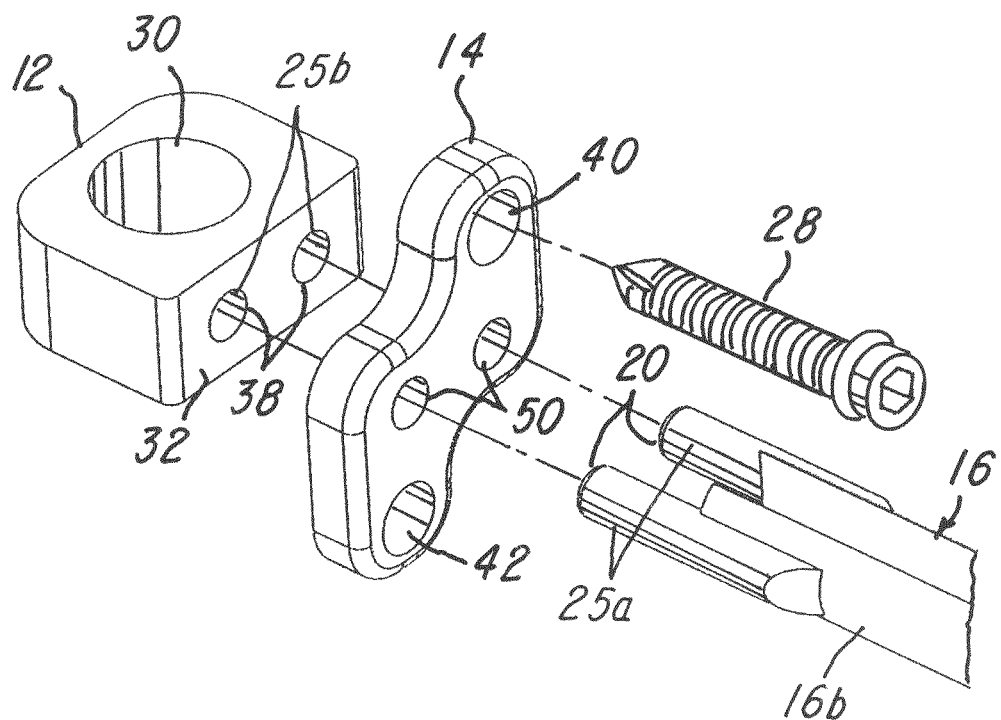

In the illustration being described and as mentioned, the second end 16b comprises an inserter fastener 20 which in the illustration being described comprises threads 22. Although the inserter fastener 20 is shown as having threads 22 in the illustration, it should be understood that the inserter fastener 20 could be any suitable means for coupling the inserter 16 to at least one of the cage 12 or plate 14 so that they may be substantially simultaneously mounted on the inserter 16 and implanted into a patient P (FIG. 1) during a surgical procedure. It should be understood that while the illustration described shows a threaded coupling between the cage 12 and inserter 16, a non-threaded fastener, coupler or coupling means may be used. For example, FIG. 7A shows a camming coupling 21a at the end 16b with a complementary coupling aperture 21b in the cage 12. FIG. 7B shows a keying connection 23a with a complementary keying coupling aperture 23b. FIG. 7C shows a spreading or clamping coupling 25a at end 16b and a complementary spreading or clamping aperture 25b.

For ease of illustration, FIG. 1 shows the inserter 16 being used to substantially simultaneously insert the cage 12 and plate 14 into the patient such that the cage 12 becomes situated between a first vertebra 24 and a second vertebra 26 as illustrated. In the illustration being described, at least one or a plurality of screws 28 may be received in at least one aperture 40 and 42 of the plate 14 and screwed into, for example, the first vertebra 24 in a manner conventionally known in order to secure the plate 14 thereto. In the illustration, the plate 14 is not secured, coupled or fixed to the cage 12 and can move, migrate or float with respect thereto. The cage 12 and plate 14 are separate components.

Figure 2:
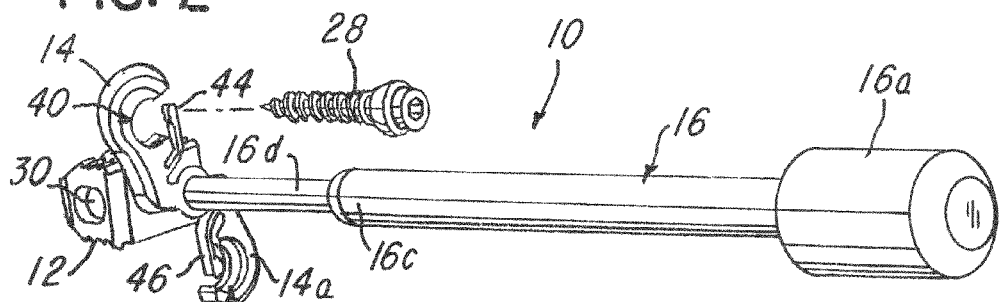
FIG. 2 is a perspective view showing the system of FIG. 1.
Figure 3:
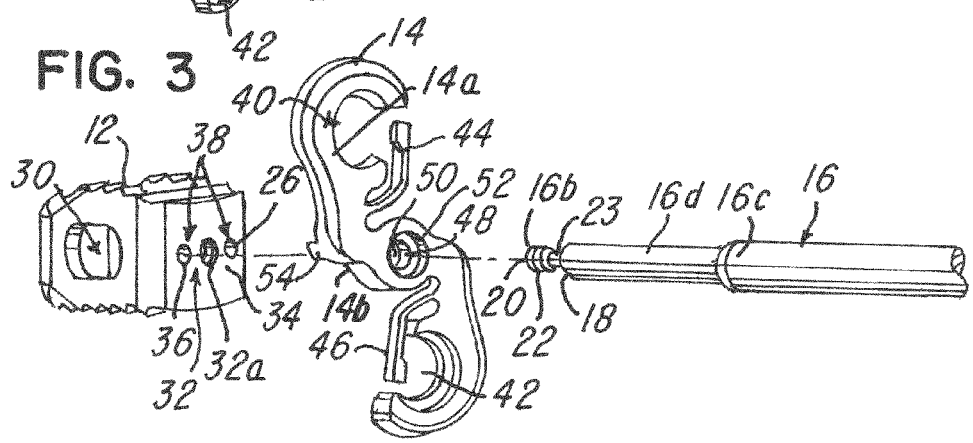
FIG. 3 is an exploded view showing the cage, plate and inserter shown in assembled form in FIGS. 1 and 2.
Figure 4:
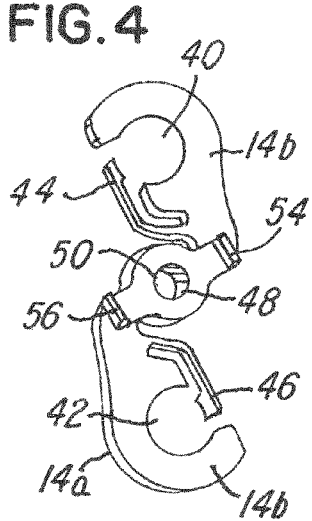
FIG. 4 is a view showing various details of the plate.

Referring now to FIGS. 2 and 4, note that the cage 12 comprises a plurality of apertures 30 through which a graft material 15 (FIG. 1) may be inserted or packed into the cage 12. The cage 12 further comprises at least one coupler 32. In the illustration being described, the at least one coupler 32 has a threaded cage wall 32a that defines a threaded opening 34 for receiving the threads 22 of the inserter 16 as illustrated in FIGS. 1-3. The at least one coupler 32 and inserter fastener 20 may be any suitable means or method for affixing a portion, such as the second end 16b, of the inserter 16 to the cage 12 after the inserter 16 has received the plate 14. While the illustration being described illustrates that the inserter fastener 20 is at the second end 16b of the inserter 16, it should be understood that it does not necessarily have to be on the second end 16b, and it could be situated at other locations on the inserter 16.

Referring back to FIG. 3, note that the cage 12 further comprises at least one or a plurality of aligning walls 36 that define at least one or a plurality of aligning apertures 38 as shown. The function and operation of the at least one or a plurality of aligning apertures 38 will be described later herein.

Referring now to FIG. 3, note that the plate 14 comprises a first side 14a and a second side 14b as shown. The plate 14 is adapted or configured to define a plurality of screw receiving openings 40 and 42 which have an associated integral lock 44 and 46, respectively. The operation of the integral lock is similar to that described in U.S. Pat. Nos. 7,182,782; 7,641,701; 7,655,028 and U.S. Patent Publications 2006/0195100; 2007/0123885; 2008/0021476 and 2010/0145453, all of which are incorporated herein by reference and made a part hereof. Features of the plates in those references may also be used in the embodiments being described.

The plate 14 has an internal wall 48 that defines a through-hole 50 for receiving the second end 16b of the inserter 16. In the illustration shown in FIG. 3, the through-hole 50 is not threaded and is sized to permit the threads 22 of inserter 16 to pass through the through-hole 50. In this regard, the second end 16b of the inserter 16 has a shank or elongated portion 25, a portion of which comprises the threads 22 and an unthreaded portion 23 as illustrated in FIG. 3. In the illustration being shown in FIG. 2, the internal wall 48 becomes operatively associated with the unthreaded portion 23 after the second end 16b is inserted in the through-hole 50 as shown.

Figure 5:
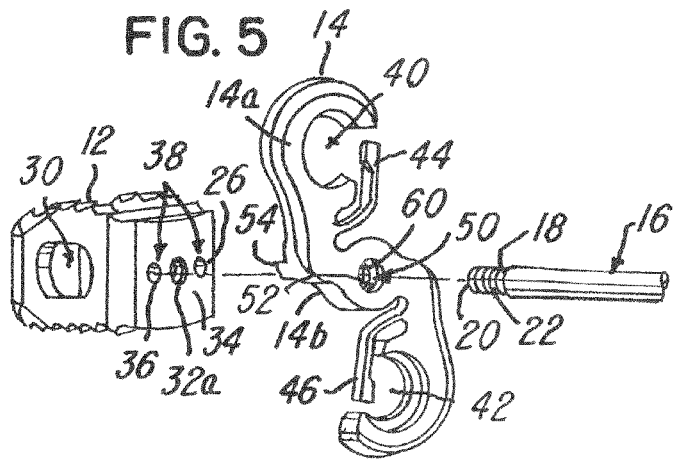
FIG. 5 is another exploded view showing the plate with a threaded aperture for threadably receiving the inserter.

As shown in FIGS. 3 and 5, the plate 14 may further comprise a receiving shoulder 52 for receiving the stop or shoulder 18 so that the plate 14 does not ride along an unthreaded shank portion or end 16d of the inserter 16.

As illustrated in FIGS. 3 and 5, the second end 16b is inserted through the through-hole 50 of the plate 14 and then screwed into the threaded opening 34 so that the plate 14 becomes secured between the stop or shoulder 18 and the cage 12 as shown. Once the cage 12, plate 14 and inserter 16 are secured together, the inserter 16 may be used to position the cage 12 between the first vertebra 24 and the second vertebra 26 and held in place while at least one screw 28 is received in the at least one aperture 40 and 42 and screwed into bone. After the plate 14 and cage 12 are operatively positioned and secured to the bone, the inserter 16 is unscrewed from the cage 12 and withdrawn from the plate 14 and the patient.

In one embodiment and in order to maintain the relationship of the cage 12 to the plate 14 during insertion, at least one of or both of the cage 12 or plate 14 may comprise at least one or plurality of aligners 54 and 56 (FIG. 4). The at least one or plurality of aligners 54 and 56 are integrally formed in the plate 14 as shown. The at least one or plurality of aligners 54 and 56 are received in the aligning apertures 38 and cause the plate 14 to be generally aligned with the cage 12 after the inserter 16 receives the plate 14 and cage 12. Of course, other means for aligning the plate 14 relative to the cage 12 may be provided.

The at least one or plurality of aligners 54 and 56 facilitate aligning the cage 12 to the plate 14 and also facilitate preventing the plate 14 or cage 12 from any rotational movement when the inserter 16 is unscrewed or dismounted from the cage 12 and plate 14. In the illustration being described, the at least one or plurality of aligners 54 and 56 are integral projections that extend away from surface 14b as shown in FIGS. 4 and 5.

FIG. 5 illustrates another embodiment wherein the plate 14 comprises an internal threaded wall 60 as shown. In this embodiment, the second end 16b of the inserter 16 has threads 22 that are long enough to screw into both the plate 14 and the cage 12 to threadably secure the cage 12 and plate 14 together.

Although the embodiments being shown and described herein illustrate various means for securing the cage 12 and plate 14 together using the threads 22 that are threadably received in at least one or both of the cage 12 and plate 14, other means for securing the inserter 16 to the cage 12 and plate 14 may be used without departing from the true spirit and scope of the invention.

The system and method 10 for co-inserting the cage 12 and plate 14 into the patient during a surgical procedure will now be described. In general, the end 16d of the inserter 16 is passed through the through-hole 50 and then screwed into the threaded opening 34 in the cage 12. Note that if the embodiment of FIG. 5 is used, then the threaded second end 16b of the inserter 16 is screwed first into the internal wall 48 of the plate 14 and then into the threaded opening 34 of the cage 12 to secure the cage 12 and plate 14 to the inserter 16. In either embodiment, the stop or shoulder 18 is received in the receiving shoulder 52 of the plate 14.

The inserter 16 substantially simultaneously receives and supports the cage 12 and plate 14 so that simultaneous implanting of the cage 12 and plate 14 using the inserter 16 can be performed during a surgical procedure. In this regard, note in FIG. 1 that the co-insertion system 10 enables the cage 12 and the plate 14 to substantially simultaneously be positioned such that the cage 12 is received in the area between the vertebra 24 and vertebra 26.

After the cage 12 and plate 14 are positioned, the inserter 16 may be unscrewed or rotated and removed from the cage 12 and plate 14. In this regard, note that the inserter 16 may be held in place while at least one of the plurality of screws 28 is used to secure the plate 14 to at least one of the vertebra 24 or 26. Thereafter, the inserter 16 may be unscrewed from the cage 12 and/or plate 14. It should be understood, therefore, that the inserter 16 is first removed from the cage 12 and then removed from the plate 14 at the end of the surgical procedure. In contrast the inserter 16 is inserted first through the plate 14 and then into the cage 12 when the inserter 16 is mounted to these components.

As alluded to earlier herein, when the inserter 16 is mounted to the cage 12 and plate 14, the at least one or plurality of aligners 54 and 56, may be used to align and maintain alignment of the cage 12 and plate 14 together.

Advantageously, the system and method 10 enable the co-insertion or substantially simultaneous insertion of the cage 12 and plate 14 using a single tool, namely, the inserter 16. In a preferred embodiment, the cage 12 is first packed or loaded with the graft material 15 (FIG. 1) either before or after the plate 14 and cage 12 are mounted on the inserter 16. Alternatively, the graft material 15 may be inserted or packed into the cage 12 after it is positioned in the patient.

Other features may include:

1. At least one or a plurality of bone-penetrating prongs (not shown) may be situated on the second side 14b of the plate 14 to penetrate the bone and facilitate stabilizing the plate 14 during or following insertion or when the inserter 16 is removed from the plate 14 and cage 12.

2. Note that the at least one or plurality of aligners 54 and 56 are illustrated as being integral with the plate 14, other types of aligners could be used and/or the aligners could be situated on or even integral with the cage 12, with the plate 14 being adapted to receive the at least one or plurality of aligners 54 and 56, such as by providing receiving apertures in the plate 14.

3. Another feature of the system and method 10 described herein is that it facilitates or enables implantation of two independent and un-coupled components, namely the cage 12 and plate 14. In this regard, even if the components comprise an aligner, the cage 12 and plate 14 are not coupled directly together in the illustrations being described. It is envisioned that this feature of the plate 14 relative to the cage 12 can be provided similar to that which is shown in U.S. Pat. No. 7,182,782, which is owned by the Assignee of the present application and which is incorporated herein by reference and made a part hereof.

4. The plate 14 may be comprised of a shortened length plate 14 which does not extend past the upper and lower borders of the cage 12.

5. The plate 14 may incorporate various screw-plate locking mechanisms to prevent rotation and/or expulsion of fixation screws 28.

6. The plate 14 may comprise various screw arrangements and/or angulations, such as one upward screw 28 or downward screw alone; one upward and one downward; two upward and one downward; one upward and two downward; or two upward and two downward or the like.

Figure 6A:
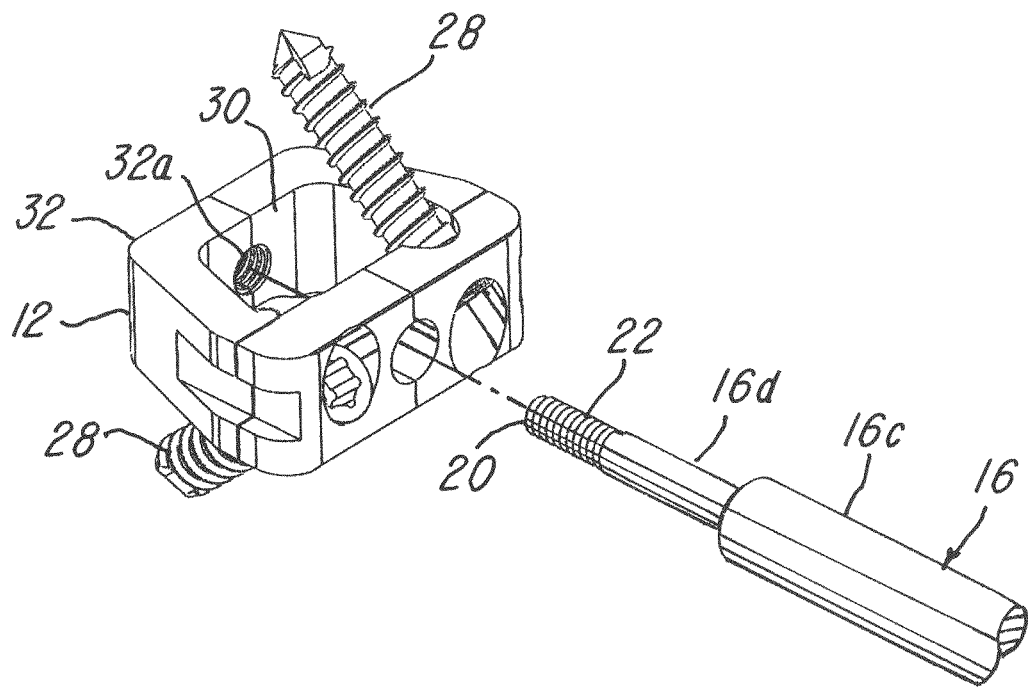
FIGS. 6A and 6B are views of an embodiment showing the inserter traversing a substantial depth of the cage and fastener to a rear wall.
Figure 6B:
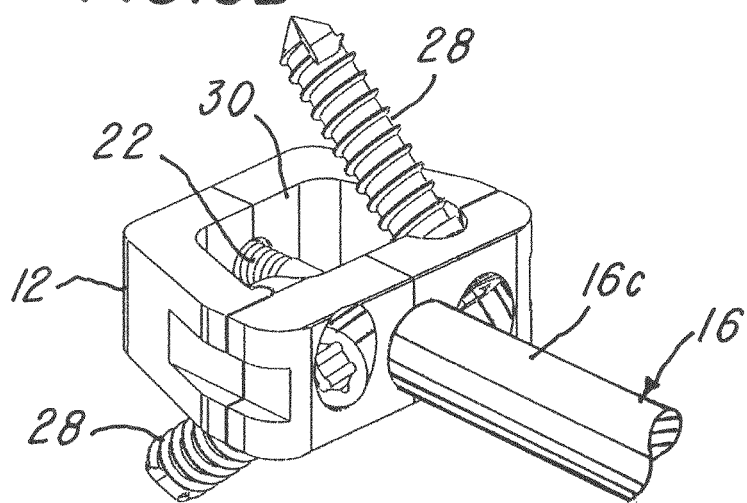

7. The cage 12 may comprise a reduced, fenestrated or eliminated front wall, such that the inserter 16 can transverse the plate 14 and a substantial depth of the cage 12 with the inserter 16 engaging a rearward wall 12a of the cage 12. This feature is illustrated in FIGS. 6A and 6B and shows the inserter 16 traversing the depth of the cage 12 so that it can fasten to a rear wall 12a of the cage 12 as shown.

8. The inserter 16 to cage 12 mechanical coupling may incorporate various fixation means mentioned earlier, such as threading, camming, keying, spreading, clamping and otherwise reversibly locking the inserter 16 to the cage 12.

In the illustrations, the components can be made from any biocompatible material. Potential biocompatible materials comprise metals (for example, titanium), metal alloys (for example, titanium alloy), carbon fibers, composites, polymers or hybrid materials.

While the system and method herein described constitute preferred embodiments of this invention, it is to be understood that the invention is not limited to this precise system and method, and that changes may be made therein without departing from the scope of the invention which is defined in the appended claims.

What is claimed is:

1. A spinal implant co-insertion system comprising:
an inserter having a handle and an inserter fastener;
a cage having at least one coupler adapted to be fastened to said inserter fastener; and
a plate;
said inserter being adapted to simultaneously receive said plate and said cage for simultaneous co-implantation of said plate and cage;
wherein said inserter fastener comprises at least one of threads, a cam, a key, a spread or a clamp, said at least one coupler of said cage being adapted to be fastened or coupled to said inserter fastener;
wherein said plate comprises an internal wall that defines a through-hole to permit said inserter fastener of said inserter to pass therethrough so that said inserter fastener can be fastened to said at least one coupler of said cage;
wherein said plate is not securely coupled or fixed to said cage so that said plate can move, migrate or float with respect to said cage after said plate and said cage are implanted;
wherein said inserter simultaneously receives said plate and cage so that while said plate and cage are simultaneously co-implanted, said plate and cage are coupled together by said inserter and after said plate and cage are implanted and said inserter is removed from said plate and cage, said cage and plate are independent, uncoupled and separate components;
wherein said internal wall of said late defines said through-hole which comprises a shape that is generally the same and complementary as a shape of said inserter fastener.

2. The spinal implant co-insertion system as recited in claim 1 wherein said inserter fastener is at an end of said inserter.

3. The spinal implant co-insertion system as recited in claim 1 wherein said plate comprises a receiving shoulder and said inserter comprises an inserter shoulder integral with said inserter fastener, said inserter shoulder engaging said receiving shoulder when said inserter fastener is coupled to said at least one coupler to facilitate maintaining said plate and said cage in a generally adjacent position during a surgical procedure.

4. The spinal implant co-insertion system as recited in claim 1 wherein said plate comprises said internal wall that is unthreaded and defines said through-hole for receiving said inserter.

5. The spinal implant co-insertion system as recited in claim 1 wherein said internal wall is threaded and said inserter fastener is threaded.

6. The spinal implant co-insertion system as recited in claim 1 wherein the end of said inserter fastener is threaded and said internal wall is threaded and adapted to threadably receive said threaded end of said inserter so that said threaded end may be screwed into both said plate and said cage.

7. The spinal implant co-insertion system as recited in claim 1 wherein said plate comprises a bone-penetrating prong to facilitate stabilizing said plate during or following insertion or when said inserter is removed from said plate and cage.

8. The spinal implant co-insertion system as recited in claim 1 wherein at least one of said cage or plate has an aligner for operatively aligning said cage and said plate together.

9. The spinal implant co-insertion system as recited in claim 8 wherein said aligner is integrally formed in said plate.

10. The spinal implant co-insertion system as recited in claim 9 wherein said aligner comprises at least one projection that causes said plate and cage to become aligned when they are received on said inserter.

11. The spinal implant co-insertion system as recited in claim 8 wherein said aligner comprises a plurality of projections that cause said plate and cage to become aligned when they are received on said inserter.

12. The spinal implant co-insertion system as recited in claim 11 wherein said cage comprises a plurality of aligning apertures for receiving said plurality of projections in order to align said cage relative to said plate.

13. A spinal implant co-insertion system, comprising: a cage having at least one coupler adapted to be fastened to an inserter having an inserter end;
a plate having a body;
said body having an internal wall that defines a through-hole for receiving said inserter having an inserter end that is screwed into said cage so that said inserter can simultaneously receive said cage and said plate so that they can be simultaneously implanted during a surgical procedure;
wherein said inserter end comprises at least one of threads, a cam, a key, a spread or a clamp, said cage being adapted to be fastened or coupled to said inserter end;
wherein said through-hole permits said inserter end of said inserter to pass therethrough so that said inserter end can be fastened to said at least one coupler of said cage;
wherein said plate is not securely coupled or fixed to said cage so that said plate can move, migrate or float with respect to said cage after said plate and said cage are implanted;
wherein said inserter simultaneously receives said plate and cage so that while said plate and cage are simultaneously co-implanted, said plate and cage are coupled together by said inserter and after said plate and cage are implanted and said inserter is removed from said plate and cage, said cage and plate are independent, uncoupled and separate components;
wherein said internal wall of said plate defines said through-hole which comprises a shape that is generally the same and complementary as a shape of said inserter end.

14. The spinal implant co-insertion system as recited in claim 13 wherein said internal wall is threaded.

15. The spinal implant co-insertion system as recited in claim 13 wherein said internal wall is threaded and adapted to threadably receive a threaded end of said inserter so that said threaded end may be screwed into both said plate and said cage.

16. The spinal implant co-insertion system as recited in claim 13 wherein said plate comprises a bone-penetrating prong to facilitate stabilizing said plate during or following insertion or when said inserter is removed from said plate and cage.

17. The spinal implant co-insertion system as recited in claim 13 wherein said plate comprises an aligner for operatively aligning said cage and said plate together.

18. The spinal implant co-insertion system as recited in claim 17 wherein said aligner is integrally formed in said plate.

19. The spinal implant co-insertion system as recited in claim 18 wherein said aligner comprises at least one projection that causes said plate and cage to become aligned when they are received on said inserter.

20. The spinal implant co-insertion system as recited in claim 17 wherein said aligner comprises a plurality of projections that cause said plate and cage to become aligned when they are received on said inserter.

21. The spinal implant co-insertion system as recited in claim 20 wherein said plurality of projections cooperate to define a receiving area for receiving and aligning said cage relative to said plate.

* * * * *

UNITED STATES PATENT AND TRADEMARK OFFICE
CERTIFICATE OF CORRECTION

PATENT NO.        : 8,945,227 B2
APPLICATION NO.   : 13/017622
DATED             : February 3, 2015
INVENTOR(S)       : Kirschman Page 1 of 1

It is certified that error appears in the above-identified patent and that said Letters Patent is hereby corrected as shown below:

In the Claims

Claim 1, Column 6, line 40, delete "late" and insert -- plate -- therefor.

Signed and Sealed this
Eighth Day of September, 2015

Michelle K. Lee
*Director of the United States Patent and Trademark Office*